United States Patent
Liu et al.

(10) Patent No.: US 9,715,744 B2
(45) Date of Patent: Jul. 25, 2017

(54) METHOD AND DEVICE OF OBTAINING BEAM HARDENING CORRECTION COEFFICIENT FOR CARRYING OUT BEAM HARDENING CORRECTION ON COMPUTED TOMOGRAPHY DATA

(71) Applicant: GE Medical Systems Global Technology Co. LLC, Waukesha, WI (US)

(72) Inventors: Dan Liu, BeiJing (CN); Xueli Wang, BeiJing (CN); Yanling Qu, Beijing (CN)

(73) Assignee: General Electric Company, Schenectady, NY (US)

( * ) Notice: Subject to any disclaimer, the term of this patent is extended or adjusted under 35 U.S.C. 154(b) by 280 days.

(21) Appl. No.: 14/567,557

(22) Filed: Dec. 11, 2014

(65) Prior Publication Data

US 2016/0171725 A1   Jun. 16, 2016

(51) Int. Cl.

| | |
|---|---|
| *G06K 9/00* | (2006.01) |
| *A61B 6/00* | (2006.01) |
| *G01N 23/00* | (2006.01) |
| *G21K 1/12* | (2006.01) |
| *H05G 1/60* | (2006.01) |
| *G01D 18/00* | (2006.01) |
| *G06T 11/00* | (2006.01) |
| *G01N 23/04* | (2006.01) |
| *A61B 6/03* | (2006.01) |

(52) U.S. Cl.
CPC ............ *G06T 11/005* (2013.01); *A61B 6/032* (2013.01); *A61B 6/5205* (2013.01); *A61B 6/5258* (2013.01); *A61B 6/583* (2013.01); *G01N 23/046* (2013.01); *G06T 2207/10081* (2013.01)

(58) Field of Classification Search
None
See application file for complete search history.

(56) References Cited

U.S. PATENT DOCUMENTS

| | | | |
|---|---|---|---|
| 2003/0161443 A1* | 8/2003 | Xiao | G06T 11/006 378/210 |
| 2004/0167387 A1* | 8/2004 | Wollenweber | A61B 6/037 600/407 |
| 2005/0123215 A1* | 6/2005 | Man | G06T 11/005 382/275 |

(Continued)

*Primary Examiner* — Matthew Bella
*Assistant Examiner* — Jose M Torres

(57) ABSTRACT

The present invention relates to a method and device of obtaining a beam hardening correction coefficient for carrying out beam hardening correction on computed tomography data. The method includes the steps of: firstly, acquiring an original reconstructed image and an original sinogram of an object of a particular size; secondly, obtaining an error-reduced sinogram after processing the original reconstructed image by error reduction; thirdly, sampling and calculating an average value of the original sinogram and an average value of the error-reduced sinogram; fourthly, optimizing the original sinogram according to the error-reduced sinogram to determine a coefficient vector of optimization function for the object of the particular size; and finally fitting the coefficient vector of the optimization function of the original sinogram to obtain the beam hardening correction coefficient for the object of the particular size.

9 Claims, 6 Drawing Sheets

(56) References Cited

U.S. PATENT DOCUMENTS

| | | | |
|---|---|---|---|
| 2005/0259780 A1* | 11/2005 | Goodgame | G06T 11/006 378/4 |
| 2007/0147580 A1* | 6/2007 | Wu | A61B 6/032 378/18 |
| 2007/0248255 A1* | 10/2007 | Chen | G06T 11/005 382/131 |
| 2007/0297656 A1* | 12/2007 | DeMan | G01N 23/046 382/128 |
| 2009/0074278 A1* | 3/2009 | Beaulieu | A61B 6/032 382/131 |
| 2011/0150305 A1* | 6/2011 | Zeng | G06T 11/005 382/131 |
| 2011/0168878 A1* | 7/2011 | Hoerndler | A61B 6/583 250/252.1 |
| 2011/0249879 A1* | 10/2011 | Wu | A61B 6/032 382/131 |
| 2012/0294503 A1* | 11/2012 | Fei | G06T 7/0081 382/131 |
| 2013/0026353 A1* | 1/2013 | Yan | A61B 6/032 250/252.1 |

* cited by examiner

METHOD AND DEVICE OF OBTAINING BEAM HARDENING CORRECTION COEFFICIENT FOR CARRYING OUT BEAM HARDENING CORRECTION ON COMPUTED TOMOGRAPHY DATA

TECHNICAL FIELD

The present invention generally relates to computer tomography (CT), and more particularly to a method and device of obtaining a beam hardening correction coefficient for carrying out beam hardening correction on computed tomography data.

BACKGROUND ART

Auxiliary diagnostic apparatuses include magnetic resonance (MR) systems, ultrasonic systems, computed tomography (CT) systems, positron emission tomography (PET) systems, nuclear medicine and other types of imaging systems.

For example, during CT X-ray imaging of a patient by a CT system, X-rays are used for imaging the features of inner structures and regions of interest (ROI) of the patient body. The imaging is performed by a CT scanner. In operation, an object is scanned for collection of original data; then an image is reconstructed after the original data are preprocessed; and post processing is further performed to improve quality of the image.

Due to spectral correlation of ray attenuation performance of a real object, in the case of polychromatic X-rays, it will be viewable that average energy of X-rays emitted by a penetrated object shifts to a higher energy value. This effect is called "beam hardening". In a reconstructed image of the object, linear and spectrum-related ray attenuation can be observed via shift relative to grey scale value in a theoretical case. Especially, grey scale value shift in the reconstructed image caused through high nuclear charge number and high-density material (such as bone) or a beam hardening virtual image causes the reconstructed image to interfere with correct judgment of the image and may cause a relevant doctor to misinterpret the image in a worst case.

In preprocessing, beam hardening correction is carried out to at least partially eliminate the virtual image. Some existing beam hardening techniques have exhibited improved uniformity for aligned scan; however, for eccentric scan, the image still shows a band-shaped artifact.

SUMMARY OF THE INVENTION

An embodiment of the present invention provides a method of obtaining a beam hardening correction coefficient for carrying out beam hardening correction on computed tomography data. The method includes the steps of: firstly, acquiring an original reconstructed image and an original sinogram of an object of a particular size; secondly, obtaining an error-reduced sinogram after processing the original reconstructed image by error reduction; thirdly, sampling and calculating an average value of the original sinogram and an average value of the error-reduced sinogram; fourthly, optimizing the original sinogram according to the error-reduced sinogram to determine a coefficient vector of optimization function for the object of the particular size; and finally fitting the coefficient vector of the optimization function of the original sinogram to obtain the beam hardening correction coefficient for the object of the particular size.

Another embodiment of the present invention provides a device of obtaining a beam hardening correction coefficient for carrying out beam hardening correction on computed tomography data. The device includes an acquiring means, an error reducing means, an averaging means, an optimizing means and a fitting means. Wherein, the acquiring means is used for acquiring an original reconstructed image and an original sinogram of an object of a particular size; the error reducing means is used for obtaining an error-reduced sinogram after processing the original reconstructed image by error reduction; the averaging means is used for sampling and calculating an average value of the original sinogram and an average value of the error-reduced sinogram; the optimizing means is used for optimizing the original sinogram according to the error-reduced sinogram to determine a coefficient vector of optimization function for the object of the particular size; and the fitting means is used for fitting the coefficient vector of the optimization function of the original sinogram to obtain the beam hardening correction coefficient for the object of the particular size.

A method of carrying out beam hardening correction on computed tomography data, wherein using a beam hardening correction coefficient is obtained according to the method of any one of claims 1 to 6 to carry out beam hardening correction on computed tomography data of other object of a particular size.

Still another embodiment of the present invention provides an apparatus of carrying out beam hardening correction on computed tomography data. The apparatus includes: a device of obtaining a beam hardening correction coefficient for carrying out beam hardening correction on computed tomography data as described above; and a correction calculating device for using the beam hardening correction coefficient to carry out beam hardening correction on computed tomography data of other object of a particular size.

A fourth embodiment of the present invention provides a computer tomography apparatus. The apparatus includes a scanning device and a processor. Wherein, the scanning device is used for scanning an object using X-rays to obtain original data for generating an original reconstructed image; and the processor is operably coupled to the scanning device and is programmable to achieve: acquiring an original reconstructed image and an original sinogram of an object of a particular size, obtaining an error-reduced sinogram after processing the original reconstructed image by error reduction, sampling and calculating an average value of the original sinogram and an average value of the error-reduced sinogram, optimizing the original sinogram according to the error-reduced sinogram to determine a coefficient vector of optimization function for the object of the particular size, and fitting the coefficient vector of the optimization function of the original sinogram to obtain the beam hardening correction coefficient for the object of the particular size.

A fifth embodiment of the present invention provides a computer program product including instructions stored in a non-volatile recording medium, which instructions, when executed in a processor, perform the steps of the method disclosed in the embodiments of the present invention.

A sixth embodiment of the present invention provides a non-volatile storage medium having stored thereon instructions, which, when executed in a processor, perform the steps of the method disclosed in the embodiments of the present invention.

BRIEF DESCRIPTION OF THE DRAWINGS

To provide a thorough understanding of the present disclosure, embodiments of the invention are described below with reference to the accompanying drawings, wherein.

DETAILED DESCRIPTION OF THE SPECIFIC EMBODIMENTS

In the following detailed description with reference to the accompanying drawings as a part thereof, the specific embodiments in which the present disclosure is implemented are illustrated. These embodiments are set forth with sufficient details to enable persons skilled in the art to carry out the present disclosure. It shall be understood that the embodiments can be combined or alternative embodiments can be used and that structural, logical and electrical modifications can be made, without departing from the scope of the various embodiments of the present disclosure. Therefore, the following detailed description shall not be interpreted as limitative, but rather as illustrative. The scope of the present invention shall be defined by the appended claims and the equivalents thereof.

Figure 1:
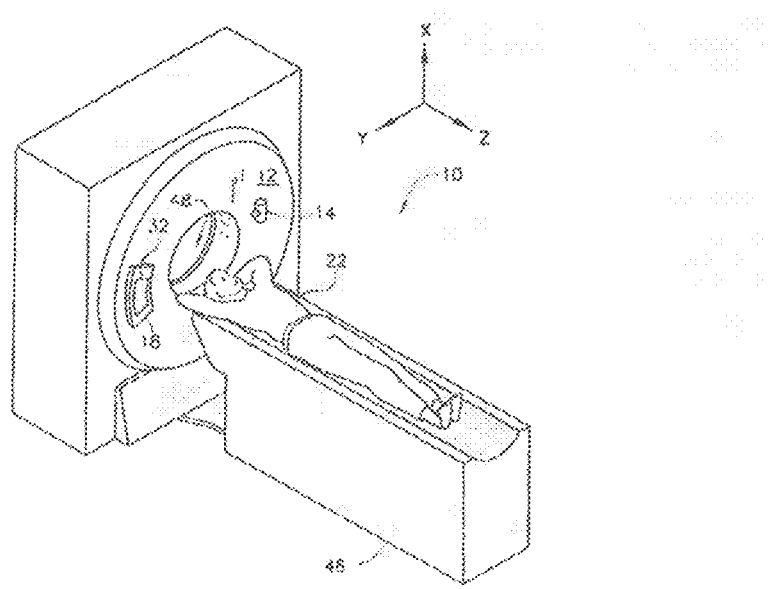
FIG. 1 is a configuration diagram of a CT imaging system according to the present disclosure.
Figure 2:
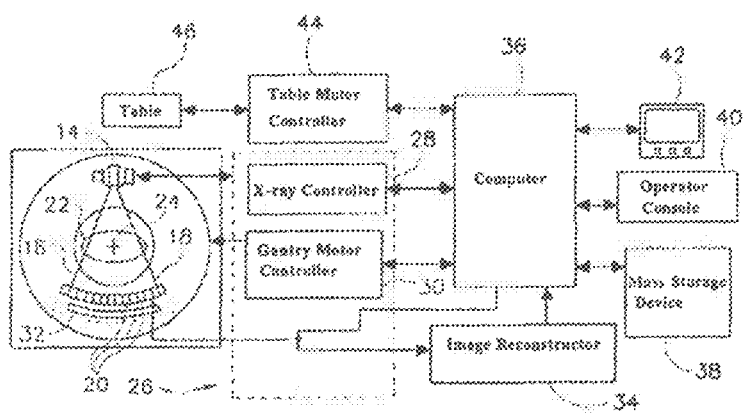
FIG. 2 is a schematic block diagram of the system shown in FIG. 1.

Referring to FIGS. 1 and 2, a CT imaging system 10 is shown as including a gantry 12. In a non-limiting embodiment, the system 10 includes a "third generation" CT scanner. The gantry 12 contains an X-ray source 14 that projects a beam of X-rays 16 towards a detector assembly 18 on the opposite side of the gantry 12. The detector assembly 18 includes a plurality of detectors 20 and a data acquisition system (DAS) 32. Said plurality of detectors 20 sense projected X-rays that pass through a medical patient 22. Each detector 20 produces an analog electrical signal that represents the intensity of the X-ray beam impinging on and hence being attenuated by the patient as it passes through the patient 22. A detector 20 typically includes a collimator for collimating the X-ray beam received at the detector, a scintillator adjacent the collimator for converting the X-ray into luminous energy, and a photodiode for receiving luminous energy from an adjacent scintillator and producing an electrical signal therefrom. Generally, each scintillator in the scintillator array converts X-rays into luminous energy and releases the luminous energy towards an adjacent photodiode. Each photodiode detects luminous energy and generates a corresponding electrical signal. Each detector 20 in the detector array 18 produces a separate electrical signal. The electrical signal represents the intensity of an impinging radiation beam (for example, an X-ray beam) and hence can be used to estimate the attenuation of the radiation beam as it passes through an object or the patient 22.

During a scan to acquire X-ray projection data, the gantry 12 and the components mounted thereon rotate around a center of rotation 24. The rotation of the gantry 12 and the operation of the X-ray source 14 can be governed by a control mechanism 26 of the CT system 10. The control mechanism 26 includes an X-ray controller 28 that provides power and timing signals to the X-ray source 14 and a gantry motor controller 30 that controls the rotational speed and position of the gantry 12. The DAS 32 in the control mechanism 26 samples analog data from the detectors 20 and converts the analog data into digital signals for subsequent processing. The output of DAS 32 includes projection data set in attenuation measurement obtained at a particular gantry rotation angle (e.g. angle of view). When the gantry 12 rotates, a plurality of views can be obtained in a single rotation. A single rotation refers to a complete 360 degree revolution of the gantry 12. Each view has a corresponding angle of view and a particular position on the gantry 12.

The reconstructed image is used as an input to a computer 36, which stores the image in a mass storage device 38.

The computer 36 also receives commands and scan parameters from an operator via an operator console 40. The operator console 40 has a certain form of operator interface, such as a keyboard, a mouse, a voice-activated controller, or any other suitable input devices. An associated display 42 allows the operator to view other data and reconstructed images from the computer 36. The commands and parameters from the operator can be used by the computer 36 to provide control signals and information to the DAS 32, the X-ray controller 28, and the gantry motor controller 30. In addition, the computer 36 operates a table motor controller 44, which controls a motorized table 46 to position the patient 22 and the gantry 12. In particular, the table 46 moves the patient 22 entirely or partially through a gantry opening 48 as shown in FIG. 1.

In one embodiment, the computer 36 includes a device 50, for example, a floppy disk drive, CD-ROM drive, DVD drive, magnetic optical disk (MOD) device, or any other digital device including a network connecting device such as an Ethernet device, for reading instructions and/or data from a computer-readable medium 52, such as a floppy disk, a CD-ROM, a DVD or another digital source such as a network or the Internet, as well as digital devices yet to be developed. In another embodiment, the computer 36 executes instructions stored in firmware (not shown). In some configurations, the computer 36 and/or image reconstructor 34 is/are programmed to execute the functions stated herein.

Figure 3:
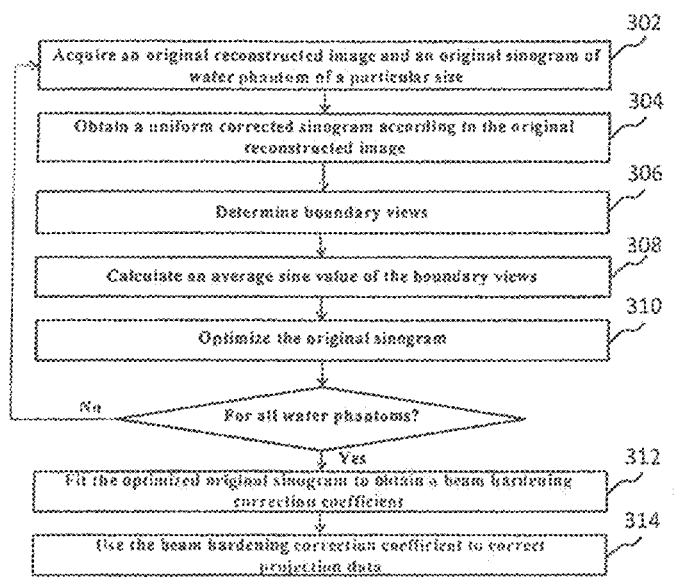
FIG. 3 is a flowchart of beam hardening correction according to an embodiment of the present disclosure.

FIG. 3 is a flowchart of beam hardening correction according to an embodiment of the present disclosure. Water phantoms of various sizes are used to calculate a beam hardening correction coefficient. However, the present invention is not limited to use of only water phantoms and applicable to use of any phantom. Water phantoms of various sizes correspond to Scan Fields of View (SFOVs) of various sizes ready to scan. Suppose that N water phantoms of different sizes are selected.

For a water phantom of a particular size, at step 302, an original reconstructed image Iorig and an original sinogram Iorig sin are acquired. The original reconstructed image Iorig and the original sinogram Iorig sin can be input after reconstruction of projection data of a DAS 32 by an image reconstructor 34; can also be acquired from a mass storage device 38; and optionally, can be acquired from a computer 36.

At step 304, orthogonal projection is implemented on the original reconstructed image, which involves a need to process the projection value by error reduction, thereby obtaining an error-reduced sinogram IUnif sin. Approaches to error reduction processing are exemplified as, yet not limited to summing CT values of pixels which X-rays detected by each detector pass through according to a view before dividing the sum by the number of pixels to obtain a value aggregate P', locating an aggregate P of projection values corresponding to the value aggregate P' in the original sinogram and using the following formula:

$$IUnif\ sin = P \times \frac{a}{P'}$$

to obtain the error-reduced sinogram IUnif sin, in which a is a fixed coefficient, for example, a value defined by a system for the water phantom.

Figure 4:
FIG. 4 is a schematic view of a method of determining a boundary view according to an embodiment of the present disclosure.
Figure 4:

Then, at step 306, boundary views are determined. In the original sinogram Iorig sin, a first view Orig_View1 where a detector channel intersects with the water phantom, for example, a view 400, is found from top to bottom; meanwhile, a first view Orig_View2 where the detector channel intersects with the water phantom in another direction, for example, a view 200, is found from bottom to top. As shown in FIG. 4, the abscissa represents the view, and the ordinate represents the detector channel. The upper line is a first horizontal line intersecting with the original sinogram from top, and the abscissa which the intersection point corresponds to represents the view 400. The lower line is a first horizontal line intersecting with the original sinogram from bottom, and the abscissa which the intersection point corresponds to represents the view 200. Similarly, views Unif_View1 (e.g., view 400) and Unif_View2 (e.g., view 200) corresponding to Orig_View1 (e.g., the view 400) and Orig_View2 (e.g., view 200) are found in the error-reduced sinogram IUnif sin.

Then, at step 308, an average sine value of the view boundaries is calculated. The original sinogram and the error-reduced sinogram need to be calculated, respectively. Firstly, sampling is required. In the original sinogram, orthogonal projection values of two boundary views and several views before and after the two boundary views are averaged. For example, as for Orig_View1, 20 views before and after Orig_View1 are identified; as for Orig_View2, 20 views before and after Orig_View2 are identified; and an average value of the orthogonal projection values of the 42 views in total is calculated to obtain an average view Orig_Aver. The same operation is applied to the error-reduced sinogram. As for Unif_View1, 20 views before and after Unif_View1 are identified; as for Unif_View2, 20 views before and after Unif_View2 are also identified; and an average value of the orthogonal projection values of the 42 views in total is calculated to obtain an average view Unif_Aver. Wherein, the averaged view number can be construed as a parameter which depends on the noise level and can be set via experimentation. The number may be 10, 20 or 40, but in an embodiment, the numbers of views taken from the two sinograms are equal.

Then, at step 310, the average view is sampled to optimize the original sinogram Iorig sin by rendering the original sinogram Iorig sin as close to the error-reduced sinogram IUnif sin as possible. The optimizing approach is shown with reference to the following formula:

$$\left| Q \times \frac{a}{Q'} - \left( Q + \sum_{i=1}^{m} \sum_{j=1}^{n} Q^i \times B_j \times b(i, j) \right) \right|^2 = 0$$

wherein, Q and Q' are Orig_Aver and Unif_Aver, respectively.

The result derived from the following formula:

$$Q \times \frac{a}{Q'}$$

is regarded as an ideal orthogonal projection value, wherein a is a fixed coefficient, for example, is a value defined by a system for the water phantom. To this end, the original orthogonal projection value P is optimized through a set of basis functions Bj (j=1, 2, . . . n, and n, as the number of the basis functions used, is also determined via experimentation). i=1, 2, . . . m. Wherein, m is a highest self-defined order. The object of this step is to determine a coefficient vector b of optimization function.

For water phantoms of different sizes, steps 302 to 310 need to be repeated, thereby determining N coefficient vectors b for N water phantoms of different sizes.

At step 312, the N coefficient vectors b are fitted to obtain a beam hardening correction coefficient c. The fitting can, for example, adopt the formula as shown below:

$$\sum_{i=1}^{m} \sum_{j=1}^{n} P^i \times B_j \times b(i, j)) = \sum_{k=1}^{h} P^k \times C_k$$

wherein, h=1, 2, . . . h, and h is a highest self-defined order, which may be the same as m or different from m.

Thereafter, the beam hardening correction coefficient vector c can be used to perform beam hardening correction on CT data of other objects of different sizes. The correction formula is similar to the formula mentioned in said fitting. The projection data after the correction Pnew are as follows:

$$P_{new} = \sum_{k=1}^{h} P^k \times C_k$$

It is to be noted that, a system needs to have the ability to perform beam hardening correction on objects of various sizes. However, in view of an individual object, as long as steps 302 to 312 are carried out only once, a beam hardening correction coefficient can be obtained for the individual object.

Figure 5:
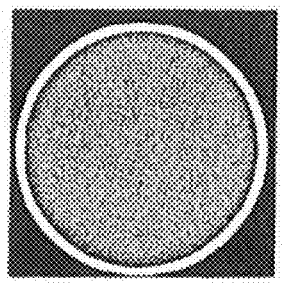
FIG. 5 is an image of water phantom reconstructed after using existing beam hardening correction.
Figure 6:
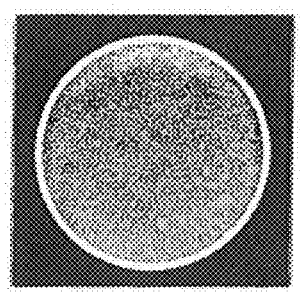
FIG. 6 is another image of water phantom reconstructed after using existing beam hardening correction.
Figure 7:
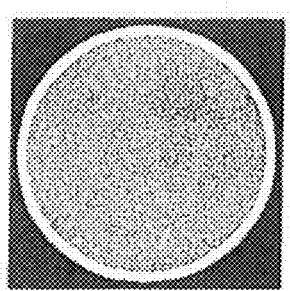
FIG. 7 is an image of water phantom reconstructed after using beam hardening correction according to an embodiment of the present disclosure.
Figure 8:
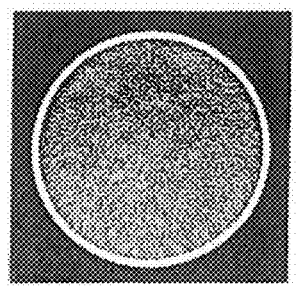
FIG. 8 is another image of water phantom reconstructed after using beam hardening correction according to an embodiment of the present disclosure.
Figure 9:
FIG. 9 is an image of skull reconstructed after using existing beam hardening correction.
Figure 10:
FIG. 10 is an image of a head phantom reconstructed after using beam hardening correction according to an embodiment of the present disclosure.

FIG. 5 is an image of water phantom reconstructed after using existing beam hardening correction, which is the result obtained from a 5.6 mm-eccentric scan. It can be seen that there is a black circle between the water phantom and the boundary, which is undesirable. FIG. 6 is another image of water phantom reconstructed after using existing beam hardening correction, which is the result obtained from a 5 cm-eccentric scan. It can be seen that, as the eccentric distance increases, the problem becomes more serious. In the image is present a wider band-shaped artifact, which is obviously undesirable. FIG. 7 is an image of water phantom reconstructed after using beam hardening correction according to an embodiment of the present disclosure, which is also obtained from a 5.6 mm-eccentric scan and in which the black circle obviously disappears. FIG. 8 is another image of water phantom reconstructed after using beam hardening correction according to an embodiment of the present disclosure, which is obtained from a 5 cm-eccentric scan. Wherein, with the band-shaped artifact disappearing, a relatively uniform image is obtained, which is desirable and in line with the actual image. Now, the result of imaging the patient's head in practice is viewable. FIG. 9 is an image of skull reconstructed after using existing beam hardening correction, which is obtained from a 5 cm-eccentric scan. It can be seen that, a band-shaped artifact is present in the skull image, which will affect the doctor's diagnosis. FIG. 10 is an image of head phantom reconstructed after using beam hardening correction according to an embodiment of the present disclosure, which is also obtained from a 5 cm-eccentric scan. It can be seen that the band-shaped artifact problem present in the image of the skull mitigates significantly. In fact, the method of the present invention is operable to eliminate or mitigate a "black circle" that may occur during a slightly eccentric scan and a band-shaped artifact that may occur during an obviously eccentric scan.

Figure 11:
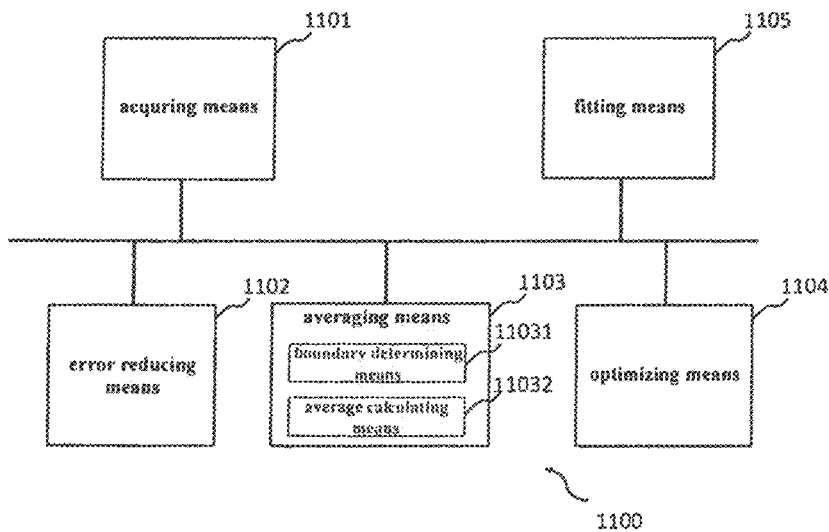
FIG. 11 is a block diagram of a device for obtaining a beam hardening correction coefficient according to an embodiment of the present disclosure.

FIG. 11 is a block diagram of a device for obtaining a beam hardening correction coefficient according to an embodiment of the present disclosure. Wherein, the device 1100 for obtaining a beam hardening correction coefficient includes: an acquiring means 1101, an error reducing means 1102, an averaging means 1103, an optimizing means 1104 and a fitting means 1105. The acquiring means 1101 is coupled to at least the error reducing means 1102, the averaging means 1103 and the optimizing means 1104. The error reducing means 1102 is coupled to at least the averaging means 1103 and the optimizing means 1104. The optimizing means 1104 is further coupled to at least the averaging means 1103 and the fitting means 1105. In FIG. 11, for convenience of illustration, all the means are coupled to each other. However, it should be noted that the all the means can be coupled to each other in any other way, as long as various function described below can be achieved. Further, functions of several of the means can be combined to be realized in one of the means; each of the means may also be further divided into more means for realization; and a same means in the system may be greater than 1 in quantity.

The acquiring means 1101 is mainly used for acquiring the original reconstructed image and the original sinogram. The error reducing means 1102 is mainly used for obtaining a relatively ideal sinogram. The averaging means 1103 is mainly used for calculating an average orthogonal projection value of the boundary view and some neighboring views of the water phantom. The optimizing means 1104 is mainly used for calculating an optimized basis function coefficient according to the result of the averaging means 1103 and the original sinogram. The fitting means 1105 is mainly used for fitting the beam hardening correction coefficient based on the results of the optimizing means 1104.

Suppose that N water phantoms of different sizes are selected. For a water phantom of a particular size, firstly, the acquiring means acquires an original reconstructed image Iorig and an original sinogram Iorig sin. The original reconstructed image Iorig and the original sinogram Iorig sin can be input after reconstruction of projection data of a DAS 32 by an image reconstructor 34; can also be acquired from a mass storage device 38; and optionally, can be acquired from a computer 36.

Then, the error reducing means 1102 implements orthogonal projection on the original reconstructed image, which involves a need to process the projection value by error reduction, thereby obtaining an error-reduced sinogram IUnif sin. Approaches to error reduction processing are exemplified as, yet not limited to summing CT values of pixels which X-rays detected by each detector pass through according to a view before dividing the sum by the number of pixels to obtain a value aggregate P', locating an aggregate P of projection values corresponding to the value aggregate P' in the original sinogram and using the following formula $$IUnif \sin = P \times \frac{a}{P'}$$

to obtain the error-reduced sinogram IUnif sin, in which a is a fixed coefficient, for example, a value defined by a system for the water phantom.

Then, the averaging means 1103 determines boundary views via a boundary determining means 11301 thereof. In the original sinogram Iorig sin, a first view Orig_View1 where a detector channel intersects with the water phantom, for example, a view 400, is found from top to bottom; meanwhile, a first view Orig_View2 where the detector channel intersects with the water phantom in another direction, for example, a view 200, is found from bottom to top. As shown in FIG. 4, the abscissa represents the view, and the ordinate represents the detector channel. The upper line is a first horizontal line intersecting with the original sinogram from top, and the abscissa which the intersection point corresponds to represents the view 400. The lower line is a first horizontal line intersecting with the original sinogram from bottom, and the abscissa which the intersection point corresponds to represents the view 200. Similarly, views Unif_View1 (e.g., view 400) and Unif_View2 (e.g., view 200) corresponding to Orig_View1 (e.g., the view 400) and Orig_View2 (e.g., view 200) are found in the error-reduced sinogram IUnif sin.

Then, the averaging means 1103 calculates an average sine value of the boundary views via an average calculating means 11302. The original sinogram and the error-reduced sinogram need to be calculated, respectively. Firstly, sampling is required. In the original sinogram, orthogonal projection values of two boundary views and several views before and after the two boundary views are averaged. For example, as for Orig_View1, 20 views before and after Orig_View1 are identified; as for Orig_View2, 20 views before and after Orig_View2 are identified; and an average value of the orthogonal projection values of the 42 views in total is calculated to obtain an average view Orig_Aver. The same operation is applied to the error-reduced sinogram. As for Unif_View1, 20 views before and after Unif_View1 are identified; as for Unif_View2, 20 views before and after Unif_View2 are also identified; and an average value of the orthogonal projection values of the 42 views in total is calculated to obtain an average view Unif_Aver. Wherein, the averaged view number can be construed as a parameter which depends on the noise level and can be set via experimentation. The number may be 10, 20 or 40, but in an embodiment, the numbers of views taken from the two sinograms are equal.

Then, the optimizing means 1104 samples the average view to optimize the original sinogram Iorig sin by rendering the original sinogram Iorig sin as close to the error-reduced sinogram IUnif sin as possible. The optimizing approach is shown with reference to the following formula:

$$\left| Q \times \frac{a}{Q'} - \left( Q + \sum_{i=1}^{m} \sum_{j=1}^{n} Q^i \times B_j \times b(i, j) \right) \right|^2 = 0$$

wherein, Q and Q' are Orig_Aver and Unif_Aver, respectively.

The result derived from $$Q \times \frac{a}{Q'}$$

is regarded as an ideal orthogonal projection value, wherein a is a fixed coefficient, for example, is a value defined by a system for the water phantom.

To this end, the original orthogonal projection value P is optimized through a set of basis functions $B_j$ (j=1, 2, ... n, and n, as the number of the basis functions used, is also determined via experimentation). i=1, 2, ... m. Wherein, m is a highest self-defined order. The object of this step is to determine a coefficient vector b of optimization function.

For water phantoms of different sizes, the above operations need to be repeated, thereby determining N coefficient vectors b for N water phantoms of different sizes. The fitting means 1105 fits the N coefficient vectors b to obtain a beam hardening correction coefficient c. The fitting can, for example, adopt the formula as shown below:

$$\sum_{i=1}^{m} \sum_{j=1}^{n} P^i \times B_j \times b(i, j)) = \sum_{k=1}^{h} P^k \times C_k$$

wherein, h=1, 2, ... h, and h is a highest self-defined order, which may be the same as m or different from m.

Thereafter, the beam hardening correction coefficient vector c can be used to perform beam hardening correction on CT data of other objects of different sizes.

Figure 12:
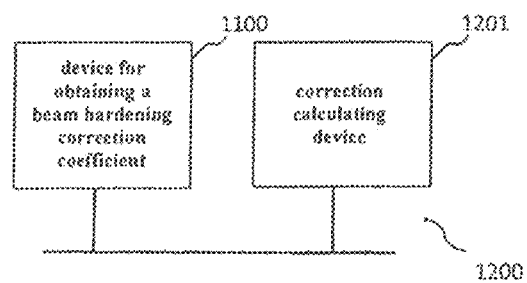
FIG. 12 is a block diagram of a device for beam hardening correction according to an embodiment of the present disclosure.

FIG. 12 is a block diagram of a device for beam hardening correction according to an embodiment of the present disclosure. Wherein, the device for beam hardening correction incudes a device 1100 for obtaining a beam hardening correction coefficient as shown in FIG. 11 and a correction calculating device 1202 connected thereto. After the device 1100 for obtaining a beam hardening correction coefficient obtains a correction coefficient vector c, the correction calculating device 1202 applies the coefficient vector c to correct the projection data p to obtain Pnew:

$$P_{new} = \sum_{k=1}^{h} P^k \times C_k.$$

As used herein, the term "a" or "an" is intended to mean both singular and plural. The term "or" means a nonexclusive or, unless otherwise indicated.

Also as used herein, the phrase "reconstructing an image" is not intended to exclude embodiments of the present invention in which data representing an image is generated instead of a viewable image. Therefore, the term "image" refers generally to viewable images and data representing a viewable image. However, many embodiments generate (or are configured to generate) at least one viewable image.

The operation environment of the present disclosure has been described with respect to a 16-slice CT system. However, one skilled in the art will appreciate that the present disclosure is also applicable to multi-slice configuration systems, and to the systems capable of moving or "jittering" focus during operation. Moreover, the present disclosure is described with regard to the detection and conversion of X-rays. However, one skilled in the art would further appreciate that the present disclosure is also applicable to detection and conversion of other high frequency electromagnetic energies. Although the specific embodiments mentioned above are described with reference to a third generation CT system, the methods described herein also apply to fourth generation CT systems (stationary detector with rotating X-ray source) and fifth generation CT systems (stationary detector and X-ray source). Additionally, it is contemplated that the benefits of the present disclosure accrue to imaging modalities other than CT, such as MRI, SPECT and PET.

Various embodiments or the components thereof may be implemented as a part of a computer system. The computer system may include a computer, an input device, a display unit and an interface, for example for accessing the Internet. The microprocessor can be connected to the communication bus. The computer may also include a memory. The memory may include a random access memory (RAM) and a read only memory (ROM). The computer system may further include a storage device, which may be a hard disk drive or a removable storage device such as a floppy disk drive and an optical drive. The storage device can also be used in other similar devices for loading computer programs or other instructions into the computer system.

In various embodiments of the present disclosure, the method of obtaining a beam hardening correction coefficient as described herein may be embodied in the form of a processor. Typical examples of processors include general purpose computers, programmed microprocessors, digital signal processors (DSPs), microcontrollers, peripheral integrated circuit elements, and other devices or equipments able to implement the method steps described herein.

As used herein, the term "computer" is not limited to those integrated circuits referred to in the art as computers, but may include any processor-based or non-processor-based systems, including systems using microcontrollers, reduced instruction set circuits (RISC), application specific integrated circuits (ASIC), logic circuits, and any other circuits or processor capable of performing the functions described herein. The above examples are exemplary only, and are not intended in any way to limit the definition and/or meaning of the term "computer". The terms such as computers, processors, microcontrollers, microcomputers, programmable logic controllers, application specific integrated circuits, and other programmable circuits are used interchangeably herein.

Processor executes a set of instructions (e.g., corresponding to the method steps), which are stored in one or a plurality of storage elements (also known as computer-usable medium). The memory element can take the form of a database or physical storage elements in the processor. The memory element can also hold as needed data or other information. Physical memory may be, for example, but not limited to, electronic, magnetic, optical, electromagnetic, infrared, or semiconductor systems, apparatuses, devices, or propagation media. More specific examples of physical memory may include, but not limited to, random access memories (RAM), read only memories (ROM), erasable programmable read-only memories (EPROM or Flash memory), hard disk drives (HDD) and CD-ROM memories (CDROM). These memory types are exemplary only, and thus the types of the memory that can be used for storing a computer program are not limitative.

The instruction set may include various commands, which instruct the processor to perform specific operations, such as the processes in various embodiments of the present invention. The instruction set may be in the form of a software program. Software may be system software or application software. In addition, the software may be an independent program, a program module in a larger program, or a set of some program modules. The software also may include a modularized program design in the form of an object-oriented programming. A processor may process input data in response to a user's command, or a result of a previous processing, or a request sent from another processor.

In various embodiments of the present invention, the method of obtaining a beam hardening correction coefficient can be implemented by software, hardware, or a combination thereof. For example, the method provided in various embodiments of the present disclosure can be implemented in software by using standard programming language (such as C, C++, Java, etc). As used herein, the terms "software" and "firmware" can be used interchangeably, and may include any computer programs stored in a memory for execution by a computer.

In addition, although the method stated herein is described with respect to a CT system used in a medical situation, it can be expected that these benefits may facilitate magnetic resonance (MR) systems, ultrasound systems, positron emission tomography (PET) systems, nuclear medicine, and other types of imaging systems. The operations can be applied to specific organs or structures, including biological organs such as brain, stomach, heart, lung or liver; biological structures, such as diaphragm, chest wall, thorax, ribs, spine, breast bone or pelvis; tumor, injury or sore, for example, compression fracture.

This written description uses examples to disclose the invention, including the preferred embodiments, and also to enable any person skilled in the art to practice the invention, including making and using any devices or systems and performing any incorporated methods. The patentable scope of embodiments of the present invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of obtaining a beam hardening correction coefficient for carrying out beam hardening correction on computed tomography data, comprising the steps of:
    acquiring an original reconstructed image and an original sinogram of an object of a particular size;
    obtaining an error-reduced sinogram after processing the original reconstructed image by error reduction;
    sampling and calculating an average value of the original sinogram and an average value of the error-reduced sinogram;
    optimizing the original sinogram according to the error-reduced sinogram to determine a coefficient vector of optimization function for the object of the particular size; and
    fitting the coefficient vector of the optimization function of the original sinogram to obtain the beam hardening correction coefficient for the object of the particular size;
    and wherein said processing the original reconstructed image by error reduction further comprises the steps of:
    summing computed tomography values of pixels which X-rays detected by each detector pass through according to a view before dividing the sum by the number of the pixels passed through to obtain a value aggregate P'; and
    locating an aggregate P of projection values corresponding to the value aggregate P' in the original sinogram and using the following formula $$P \times \frac{a}{P'}$$

to obtain the error-reduced sinogram, wherein a is a coefficient defined by a system for said object of the particular size;
    and wherein said sampling and calculating the average value of the original sinogram and the average value of the error-reduced sinogram further comprises the steps of:
    determining a boundary view of the original sinogram and a neighboring view of the original sinogram, as a first sampling view, and determining a boundary view of the error-reduced sinogram and a neighboring view of the error-reduced sinogram as a second sampling view; and
    calculating an average value of the first sampling view and an average value of the second sampling view respectively, as the average value of the original sinogram and the average value of the error-reduced sinogram.

2. The method of obtaining the beam hardening correction coefficient for carrying out beam hardening correction on computed tomography data as claimed in claim 1, wherein coefficient vectors of optimization function can be calculated for objects of different sizes, respectively, and said fitting is directed to all the coefficient vectors of the optimization function.

3. The method of obtaining the beam hardening correction coefficient for carrying out beam hardening correction on computed tomography data as claimed in claim 1, wherein said optimizing the original sinogram according to the error-reduced sinogram further comprises the step of:
    calculating a coefficient vector b making the value of $$\left| Q \times \frac{a}{Q'} - \left( Q + \sum_{i=1}^{m} \sum_{j=1}^{n} Q^i \times B_j \times b(i, j) \right) \right|^2$$

as close to zero as possible, wherein a is a fixed coefficient, Q and Q' are the average value of the original sinogram and the average value of the error-reduced sinogram, respectively, $B_j$ is basis function used, j=1, 2, . . . n, n is the number of basis functions used, i=1, 2, . . . , m, and m is a highest order defined.

4. The method of obtaining the beam hardening correction coefficient for carrying out beam hardening correction on computed tomography data as claimed in claim 3, wherein said fitting the coefficient vector of the optimization function of the original sinogram further comprises:
calculating a beam hardening correction vector c according to the formula $$\sum_{i=1}^{m}\sum_{j=1}^{n} P^i \times B_j \times b(i,j)) = \sum_{k=1}^{h} P^k \times C_k$$

wherein k=1, 2, . . . h, and h is a highest order defined and P is an aggregate of projection values corresponding to the value P' in the original sinogram.

5. A device for obtaining a beam hardening correction coefficient for carrying out beam hardening correction on computed tomography data, comprising:
an acquiring device for acquiring an original reconstructed image and an original sinogram of an object of a particular size;
an error reducing device for obtaining an error-reduced sinogram after processing the original reconstructed image by error reduction;
an averaging device for sampling and calculating an average value of the original sinogram and an average value of the error-reduced sinogram;
an optimizing device for optimizing the original sinogram according to the error-reduced sinogram to determine a coefficient vector of optimization function for the object of the particular size; and
a fitting device for fitting the coefficient vector of the optimization function of the original sinogram to obtain the beam hardening correction coefficient for the object of the particular size;
and wherein said error reducing device is further operable to:
sum computed tomography values of pixels which X-rays detected by each detector pass through according to a view before dividing the sum by the number of the pixels passed through to obtain a value aggregate P'; and
locate an aggregate P of projection values corresponding to the value aggregate P' in the original sinogram and using the following formula $$P \times \frac{a}{P'}$$

to obtain the error-reduced sinogram, wherein a is a coefficient defined by a system for said object and
wherein said averaging device is further operable to:
determine a boundary view of the original sinogram and a neighboring view of the original sinogram as a first sampling view, and determine a boundary view of the error-reduced sinogram and a neighboring view of the error-reduced sinogram as a second sampling view; and
calculate an average value of the first sampling view and an average value of the second sampling view respectively as the average value of the original sinogram and the average value of the error-reduced sinogram.

6. The device for obtaining the beam hardening correction coefficient for carrying out beam hardening correction on computed tomography data as claimed in claim 5, wherein coefficient vectors of optimization function can be calculated for objects of different sizes, respectively, and said fitting device fits all the coefficient vectors of the optimization function.

7. The device for obtaining the beam hardening correction coefficient for carrying out beam hardening correction on computed tomography data as claimed in claim 5, wherein said optimization device is further operable to:
calculate a coefficient vector b making the value of $$\left| Q \times \frac{a}{Q'} - \left( Q + \sum_{i=1}^{m}\sum_{j=1}^{n} Q^i \times B_j \times b(i,j) \right) \right|^2$$

as close to zero as possible, wherein a is a fixed coefficient, Q and Q' are the average value of the original sinogram and the average value of the error-reduced sinogram, respectively, $B_j$ is basis function used, j=1, 2, . . . n, n is the number of basis functions used, i=1, 2, . . . , m, and m is a highest order defined.

8. The device for obtaining the beam hardening correction coefficient for carrying out beam hardening correction on computed tomography data as claimed in claim 7, wherein said fitting device is further operable to:
calculate a beam hardening correction vector c according to the formula $$\sum_{i=1}^{m}\sum_{j=1}^{n} P^i \times B_j \times b(i,j)) = \sum_{k=1}^{h} P^k \times C_k$$

wherein k=1, 2, . . . h, and h is a highest order defined and P is an aggregate of projection values corresponding to the value P' in the original sinogram.

9. The device for obtaining the beam hardening correction coefficient for carrying out beam hardening correction on computed tomography data as claimed in claim 5, further comprising a correction calculating device configured to use the beam hardening correction coefficient to carry out beam hardening correction on computed tomography data of at least one other object of a particular size.

* * * * *